(12) United States Patent
Stickel et al.

(10) Patent No.: US 6,168,240 B1
(45) Date of Patent: Jan. 2, 2001

(54) ATMOSPHERIC DETECTION SYSTEM FOR AN AUTOMATED MINING SYSTEM

(75) Inventors: Danny L. Stickel, Jane Lew, WV (US); Patrick E. Retzer, Greensboro, PA (US)

(73) Assignee: Archveyor Pty Ltd., North Sydney ( * ) Notice: Under 35 U.S.C. 154(b), the term of this patent shall be extended for 0 days.

(21) Appl. No.: 09/037,614

(22) Filed: Mar. 10, 1998

(51) Int. Cl.$^7$ .............................. E21C 35/22; E21C 35/04
(52) U.S. Cl. ............................................................ 299/12
(58) Field of Search ........................... 73/23.31; 299/1.4, 299/12, 30, 1.9

(56) References Cited

U.S. PATENT DOCUMENTS

| | | | |
|---|---|---|---|
| 3,683,255 | * | 8/1972 | Schroeder ........................... 299/12 X |
| 4,281,876 | * | 8/1981 | Lansberry .............................. 299/1.4 |
| 4,323,280 | * | 4/1982 | Lansberry et al. ..................... 299/1.4 |
| 4,388,822 | * | 6/1983 | Heller ..................................... 73/23.2 |
| 4,465,318 | * | 8/1984 | Lewis et al. ....................... 299/12 X |
| 5,667,279 | | 9/1997 | Christopher et al. ................. 299/1.9 |
| 5,820,223 | * | 10/1998 | Marshall et al. ........................ 299/12 |

FOREIGN PATENT DOCUMENTS

3243542 * 5/1984 (DE) ...................................... 299/12
2234617 * 2/1991 (GB) ...................................... 299/30

OTHER PUBLICATIONS

"Installation and Operating Data", Trolex Ltd. (33 pages), undated.

* cited by examiner

Primary Examiner—Eileen D. Lillis
Assistant Examiner—Sunil Singh
(74) Attorney, Agent, or Firm—Senniger, Powers, Leavitt & Roedel

(57) ABSTRACT

An atmospheric detection system for use in a mine that includes a continuous miner used in highwall applications. The continuous miner includes a rotary cutter head attached to a frame and one or more motors for driving the rotary cutter head. A methane sensor adapted to detect an atmospheric condition is mounted to the continuous miner and positioned in close proximity to the rotary cutter head. A display is coupled to the methane sensor for displaying the atmospheric condition of the mine at a location remote of the methane sensor. A tramming conveyor and a load-out vehicle can be coupled to the continuous miner. The atmospheric detection system is adapted to be used in an underground mine where the continuous miner is positioned in a portion of the mine having an unsupported roof. The atmospheric detection system can be used in wing mining applications as well as highwall mining applications.

13 Claims, 4 Drawing Sheets

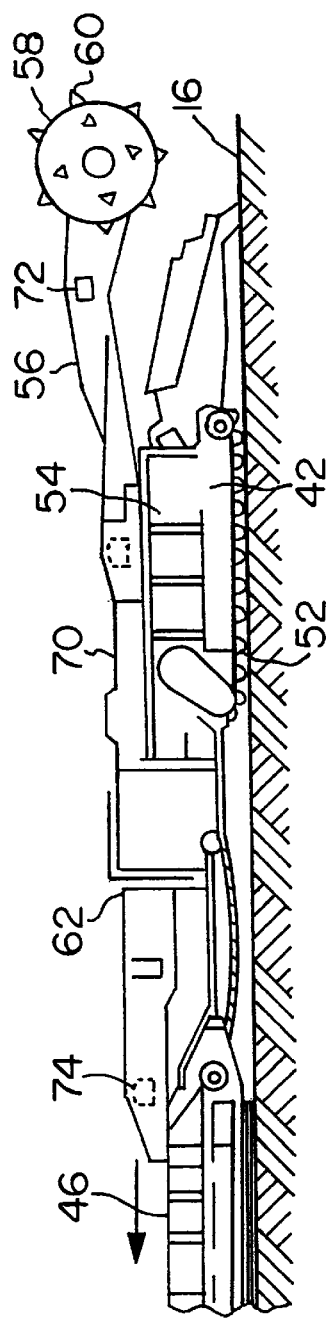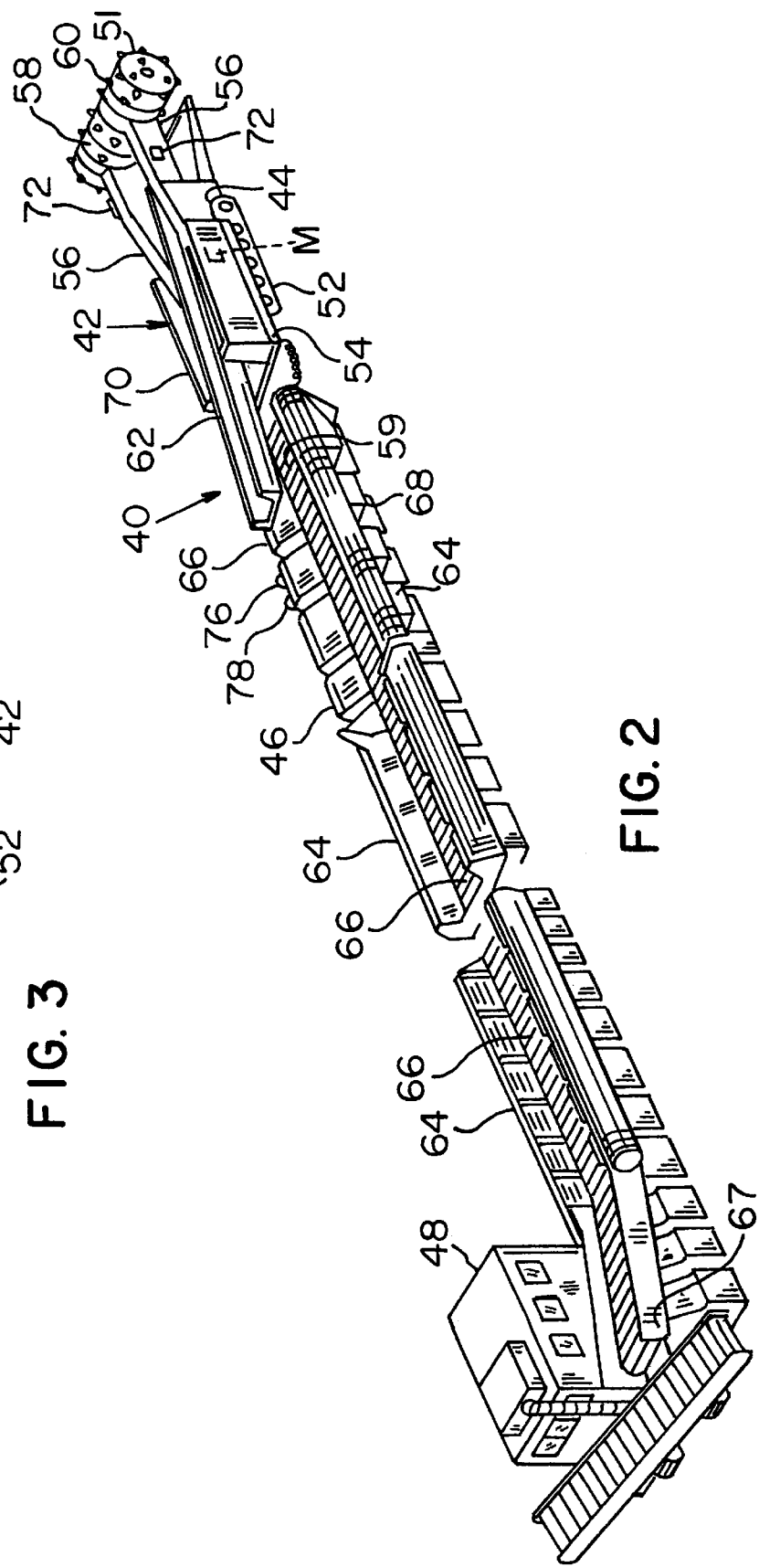

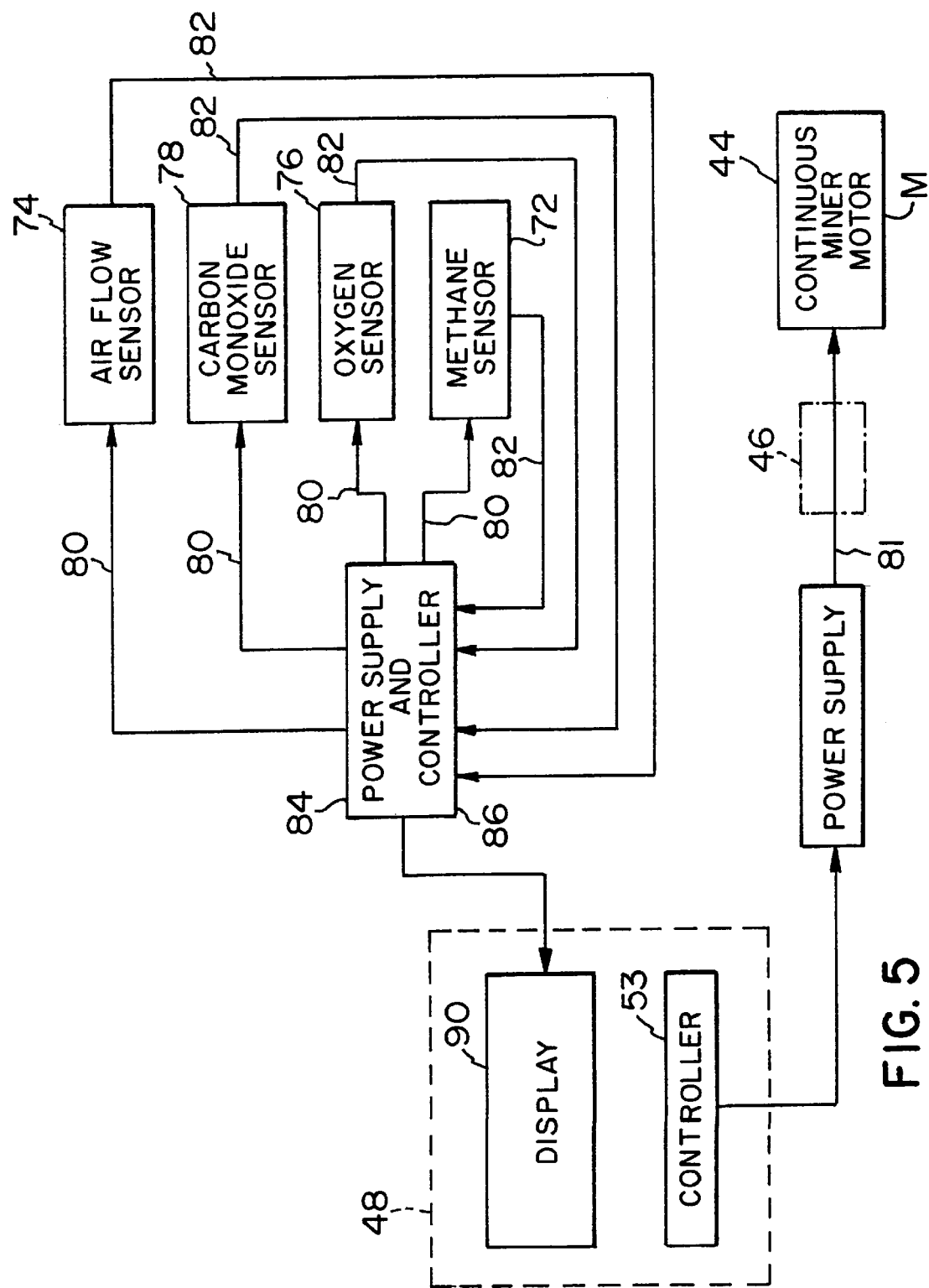

ATMOSPHERIC DETECTION SYSTEM FOR AN AUTOMATED MINING SYSTEM

BACKGROUND OF THE INVENTION

1. Field of the Invention

The present invention relates generally to atmospheric detection in an underground mine and, more particularly, measuring the presence of methane gas near a mine face during continuous mining operations.

2. Description of the Prior Art

Coal is typically found in substantial horizontal seams extending through rock strata, such as limestone, sandstone or shale. Surface mining and underground mining are the primary methods used to mine coal. Surface mining may be strip mining which involves the removal of the overburden by means of a dragline or other earth moving equipment to fully expose the coal seam for recovery. However, strip mining is limited by the depth of the overburden which eventually makes strip mining impractical. When the depth of the overburden makes strip mining impractical, a large quantity of coal may remain in the seam. Recovery of this coal is accomplished by highwall mining, wherein an entry or a hole is initiated at the exposed face of the seam at the highwall, and mining follows the seam inwardly from the highwall forming a bore. One particularly successful and innovative apparatus for continuously mining coal by highwall mining is the ARCHVEYOR® continuous mining apparatus as described in U.S. Pat. No. 5,667,279, which is hereby incorporated by reference.

The ARCHVEYOR® continuous mining apparatus includes a continuous miner, a tramming conveyor and a load-out vehicle. A bolter car may be positioned between the continuous miner and the tramming conveyor. The miner mines coal at a mine face. The mined coal is conveyed to the tramming conveyor and deposited onto a transverse conveyor. The transverse conveyor then deposits the mined coal into hopper cars or trucks for transport. An operator located in the load-out vehicle controls the operation of the continuous miner and the tramming conveyor.

A constant concern in any underground mining operation is the buildup of methane gas. Where human miners are involved, continuous monitoring of methane, as well as oxygen and carbon monoxide, is monitored to ensure safe operating conditions. Mine Safety Health Administration of the United States Department of Labor (MSHA) sets forth the rules and regulations for monitoring the methane gas levels in mines. In the case of highwall mining, MSHA does not require monitoring of the methane gas levels at the mine face using the ARCHVEYOR® continuous mining apparatus because all people involved in the mining operation are positioned outside the underground bore formed by the continuous miner. In other words, the load-out vehicle and the operator are located outside the underground bore.

However, in other applications of continuous mining, such as wing mining where humans are positioned underground, constant monitoring must be conducted near the mine face. The ARCHVEYOR® continuous mining apparatus can be used in this application. On a typical miner section, a bolter car may also be provided for installing mine roof bolts and support plates behind the continuous miner. Typically, the bolter car is positioned approximately forty feet behind the continuous miner. The bolter car installs the mine roof bolts and the bearing plates in the mine roof approximately forty feet behind the mine face. Hence, the mine shaft formed by the continuous miner has a supported roof at a distance beyond forty feet of the mine face and an unsupported roof at a distance less than forty feet toward the mine face.

Until recently, MSHA permitted methane gas levels to be measured at the last row of permanent support in the face area of the mine during continuous mining applications as shown in FIG. 1. Specifically, FIG. 1 shows a mine shaft 10 defined by two spaced apart ribs or walls 12 (only one of which is shown), a mine roof 14, a mine floor 16 and a mine face 18. The mine roof 14 has a supported portion 20 beyond a distance X measured from the mine face 18 and an unsupported portion 22 the distance X as measured toward the mine face 18. Under the previous MSHA rules, a miner 24 would monitor the gas levels of the mine shaft 10 at the distance X using a hand-held gas detector 26. Typically, under the MSHA rules, continuous mining stopped and then the miner 24 took gas readings using the detector 26 every twenty minutes. If the methane gas reading was unacceptable (too high), then mining was stopped until the methane gas level was reduced. As should be evident, this procedure puts the miner 24 at risk and adds to the cost of extracting coal since the continuous miner must be stopped every twenty minutes. Some continuous miners include a methane sensor coupled to a display attached to the continuous miner in series. If the methane sensor measures a level above a certain level, say 2%, then all power to the sensor and the continuous miner is cut off. During the period of time between shutdown and reactivation, which requires a miner 24 to enter the mine shaft 10 to restart the continuous miner, the sensor cannot measure methane levels. This arrangement places the miner 24 at great risk since gas levels are not known. Further, even during extended cut operations, the monitor cannot be read since it is positioned under the unsupported portion 22.

Recently, MSHA changed the rules for measuring gas levels in mining. Specifically, pursuant to 30 C.F.R. §§ 75.323(b)(1) and (2) and 75.362(d)(1), MSHA now requires that methane gas readings be taken in close proximity of the mine face 18. However, under MSHA rules, the miner 24 can be no closer to the mine face 18 than under the old MSHA rules due to the unsupported roof conditions. To comply with these new MSHA rules, the detectors 26 have been fitted with probe extensions 28, shown in phantom in FIG. 1. The probe extensions 28 have a length X of approximately forty feet so that gas readings can be taken at the mine face 18. This arrangement is extremely cumbersome and time consuming to use. Further, this method for measuring methane gas near the mine face 18 yields inaccurate results since it has been found that methane gas levels decrease when the mine face is not being worked by the continuous miner.

Therefore, it is an object of the present invention to safely measure gas levels near a mine face without interrupting mining by a continuous miner.

SUMMARY OF THE INVENTION

The present invention is an atmospheric detection system for use in a mine that includes a continuous miner, a sensor adapted to detect an atmospheric condition, a controller and a display. The continuous miner includes a rotary cutter head attached to a frame and a motor for driving the rotary cutter head. The sensor is mounted to the continuous miner. A first power line is provided for supplying the power to the motor. The controller is coupled to the motor and the first power line for controlling rotation of the rotary cutter head at a remote location. A second power line is provided for supplying power to the sensor. The monitor is coupled to the sensor for detecting the atmospheric condition at a location remote of the sensor. The sensor is positioned in close proximity to the rotary cutter head. Preferably, the rotary cutter head is rotatably coupled to a boom that is pivotally mounted to the frame. The sensor can be mounted to the boom.

The continuous miner can include a miner conveyor in fluid communication with the rotary cutter head and an arrangement for moving along a mine floor. A tramming conveyor can be coupled to the continuous miner. The tramming conveyor includes a conveyor in fluid communication with the miner conveyor. The tramming conveyor is also operatively coupled to the controller for controlling movement of the tramming conveyor along a mine floor and movement of the tramming conveyor. An operator station can be provided where the controller and the display are positioned therein. Preferably, the sensor is a methane sensor. The methane sensor can continuously or intermittently detect methane levels. Additional sensors can be provided, such as an air flow sensor, an oxygen sensor and a carbon monoxide sensor, which are coupled to the gas detecting system for detecting the conditions in the atmosphere.

The present invention is also a method for atmospheric detection near a face of an underground mine during operation of a continuous miner under an unsupported portion of a mining roof. The method includes the steps of: providing a continuous miner having a rotary cutter head in an underground mine having a roof, spaced apart mine ribs, a mine roof floor and a mine face, wherein the mine roof is supported by a support arrangement, such as mine roof bolts and support plates a fixed distance X from the mine face; providing an atmospheric sensor on the continuous miner which is positioned below an unsupported portion of the mine roof less than the distance X from the mine face; rotating the rotary cutter head; forcing the rotary cutter head into the mine face; extracting a mine product from the mine face; measuring the atmospheric condition in an area near the mine face in an unsupported roof portion of the mine; and detecting the atmospheric condition from a remote location in a supported roof portion of the mine or outside the mine.

BRIEF DESCRIPTION OF THE DRAWINGS

FIG. 2 is a broken top perspective view of an atmospheric detection system mounted on a continuous miner made in accordance with the present invention;

FIG. 3 is an elevation of a portion of the atmospheric detection system shown in FIG. 2;

FIG. 5 is a schematic diagram of the atmospheric detection system for a continuous miner made in accordance with the present invention;

DESCRIPTION OF THE PREFERRED EMBODIMENT

Figure 1:
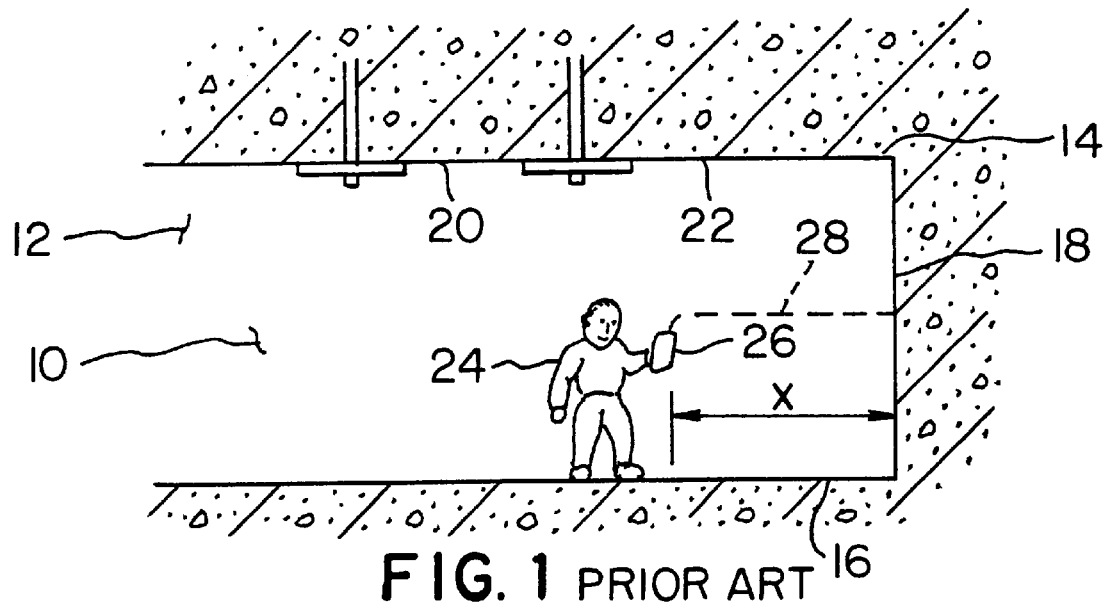
FIG. 1 is a section of a mine shaft with a miner taking gas measurements according to the prior art.

FIG. 2 shows an atmospheric detection system 40 for use in a mine made in accordance with the present invention. The atmospheric detection system 40 includes a continuous mining apparatus 42, such as an ARCHVEYOR® continuous mining apparatus described in U.S. Pat. No. 5,667,279, which is generally described as follows.

The continuous mining apparatus 42 includes a continuous miner 44 coupled to a tramming conveyor 46 and a load-out vehicle or operator station 48. A bolter car (not shown) can be provided and positioned between the continuous miner 44 and the tramming conveyor 46. The continuous miner 44 includes a forward end 51 and crawlers 52 attached to a frame 54. Wheels or any other type of arrangement can be provided which permit the miner 24 to move along the mine floor 16. A rotary cutter head 58 having bits 60 is rotatably attached or coupled to a boom 56 which is pivotally attached or mounted to the frame 54. An electric motor M or a plurality of motors is provided which rotates the rotary cutter head 58. A discharge conveyor or miner conveyor 62 is attached to the frame 54 having one end in close proximity to and in fluid communication with the rotary cutter head 58. The other end is adjacent to and in fluid communication with an inlet end or inby end 59 of the tramming conveyor 46. The inlet end 59 is also positioned adjacent the continuous miner 44. The tramming conveyor 46 includes a plurality of separately driven sections 64, that when connected, form a continuous conveyor. Electric motors provide for the movement of the sections 64 and the conveyor 66. An outlet end or outby end 67 of the tramming conveyor 46 is in fluid communication with the load-out vehicle 48. The outlet end 67 is positioned adjacent the load-out vehicle 48. The load-out vehicle 48 is operatively connected or coupled to the continuous miner 44, the tramming conveyor 46 through electrical connections, computer controls and controllers 53 for controlling the movement of the continuous miner 44 and the tramming conveyor 46 along the mine floor 16 and movement of the conveyor 66 and the discharge conveyor 62. A human operator or technician operates the continuous mining apparatus 42 from within the load-out vehicle 48 at a remote location from the continuous miner 44 in the supported portion 20 of the mine shaft 10 or external of the mine shaft 10. A ventilation tube 68 attaches to the tramming conveyor 46. An exhaust fan 69 is provided on a scrubber 70 provided on the continuous miner 44 when used in an underground system. The scrubber 70 filters air from the mine removing particulate matter, i.e., dust, from the air during mining operations. In underground mining applications, the load-out vehicle 48 is replaced by a control cab (not shown) and a stationary belt conveyor (not shown). The control cab includes all of the controls and monitors of the load-out vehicle 48 and receives an operator or technician to control mining. The size of the control cab is such that it can be received in a mine shaft and can be positioned remote of the tramming conveyor 46 and the continuous miner 44. The belt conveyor is positioned parallel to the tramming conveyor 46. Mined coal is transferred from the tramming conveyor 46 to the stationary belt conveyor through a transfer section (not shown).

The present invention includes two methane sensors 72 mounted to the continuous miner 44. Both methane gas sensors 72 are provided on or mounted to the boom 56 in close proximity to the rotary cutter head 58, for example, a distance of thirty inches or less, and rearwardly of the forward end 51. One methane sensor 72 that works well in this environment is a TX3266 sensor manufactured by Trolex Limited, Newby Road, Hazel Grove, Stockport, Cheshire SK7 5DY, United Kingdom.

Figure 6A:
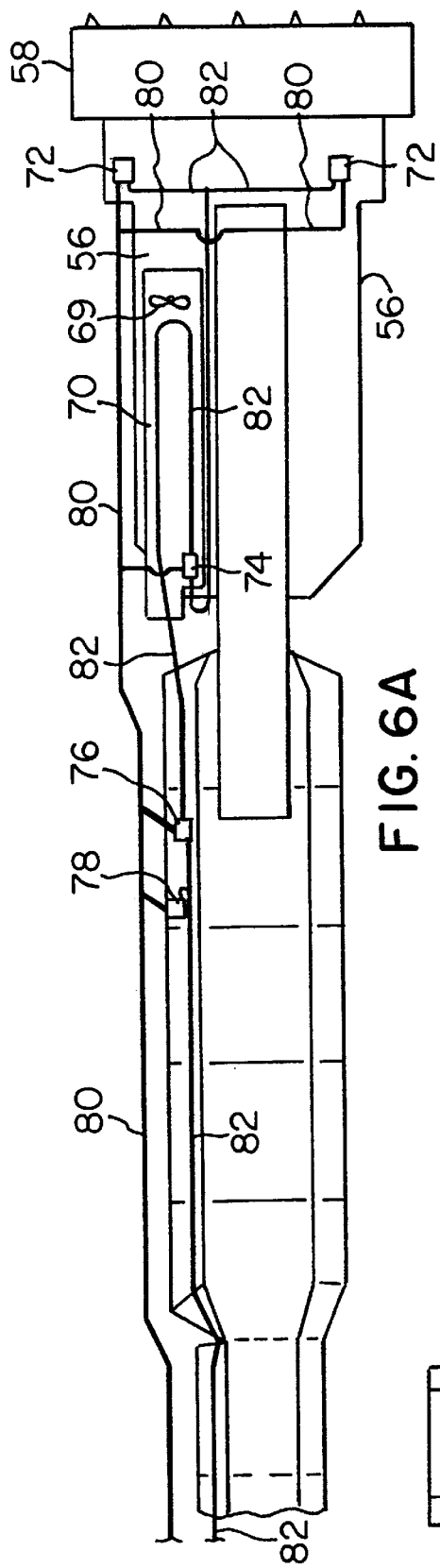
FIG. 6A is a top plan view of a portion of the atmospheric detection system mounted on the continuous miner shown in FIG. 2.
Figure 6B:
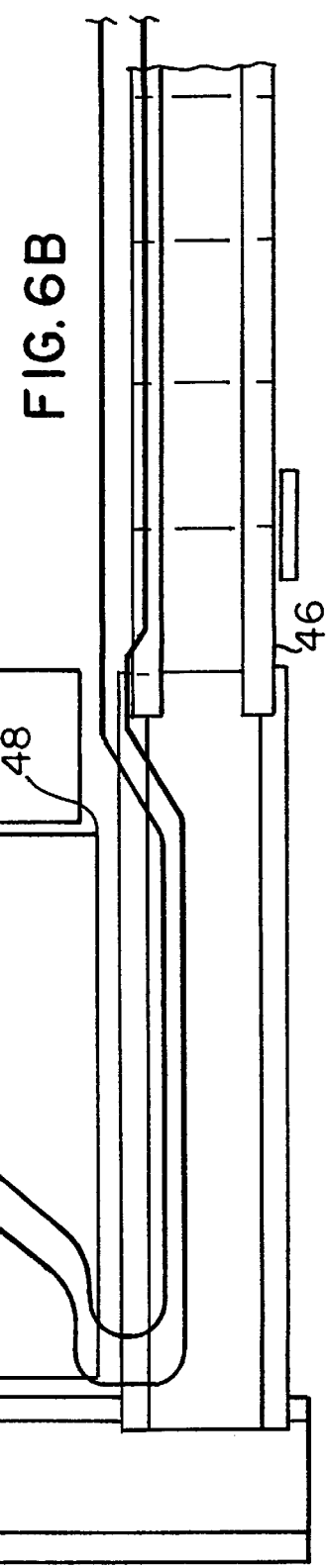
FIG. 6B is a top plan view of another portion of the atmospheric detection system mounted on the continuous miner shown in FIG. 2.

Referring to FIGS. 2–6B, additional sensors can also be provided, such as an air flow sensor 74, which measures air velocity (as shown in FIG. 6A) provided within the scrubber 70, an oxygen sensor 76 and a carbon monoxide sensor 78 provided on the tramming conveyor 46. A second air flow sensor can be provided on the air discharge end of the air intake. Trolex Limited also manufactures one type of oxygen sensor 76 and carbon monoxide gas sensor 78 under Model Nos. TX3269 and TX3256, respectively. The air flow sensor 74 measures the air velocity exiting the mine shaft 10 through the scrubber 70. Trolex Limited vortex air flow sensor Model No. TX1327 or TX1329 can be used for this application. The oxygen sensor 76 measures the gaseous oxygen at a location adjacent the oxygen sensor 76. Likewise, the carbon monoxide sensor 78 measures the carbon monoxide at a location adjacent the carbon monoxide sensor 78. The methane sensor 72, the air flow sensor 74, the oxygen sensor 76 and the carbon monoxide sensor 78 are powered by a separate power line 80 or separate power lines, as shown in FIGS. 6A and 6B, than the power line 81 represented in FIG. 5 that supplies power to the continuous miner 44 and the tramming conveyor 46. Preferably, the air flow sensor 74, the oxygen sensor 76 and the carbon monoxide sensor 78 are positioned rearwardly of the methane sensor 72. Separate cables 82 are coupled to the sensors 72, 74, 76 and 78, which are then coupled to a microprocessor based controller 84 for reading, detecting, monitoring and/or analyzing information relating to atmospheric conditions near the mine face 18, namely, methane gas, air flow, oxygen and carbon monoxide measurements taken from the sensors 72, 74, 76 and 78, respectively. A separate power supply 86 is coupled to the controller 84 for supplying power to the sensors 72, 74, 76 and 78. The information can then be printed out or displayed on a display 90 contained within the load-out vehicle 48, which is at a remote location from the sensors 72, 74, 76 and 78 for the operator or technician to observe or monitor the atmospheric conditions. This arrangement also permits detecting the atmospheric condition at a location remote of the sensors 72, 74, 76 and 78 by the controller 84, the display 90 and/or the operator or technician. Other sensors may also be added. Alternatively, separate power supplies can be provided, a twenty-four volt dc power supply for the air flow sensor 74, oxygen sensor 76 and carbon monoxide sensor 78, and a twenty volt dc power supply for the methane sensors 72. The air flow sensor 74, the oxygen sensor 76 and the carbon monoxide sensor 78 can be directly attached to the continuous miner 44 or attached to the continuous miner 44 through one of the other vehicles, such as the tramming conveyor 46. The controller 84 detects the atmospheric condition of the sensors 72, 74, 76 and 78 and relays that information to the display 90.

Figure 4:
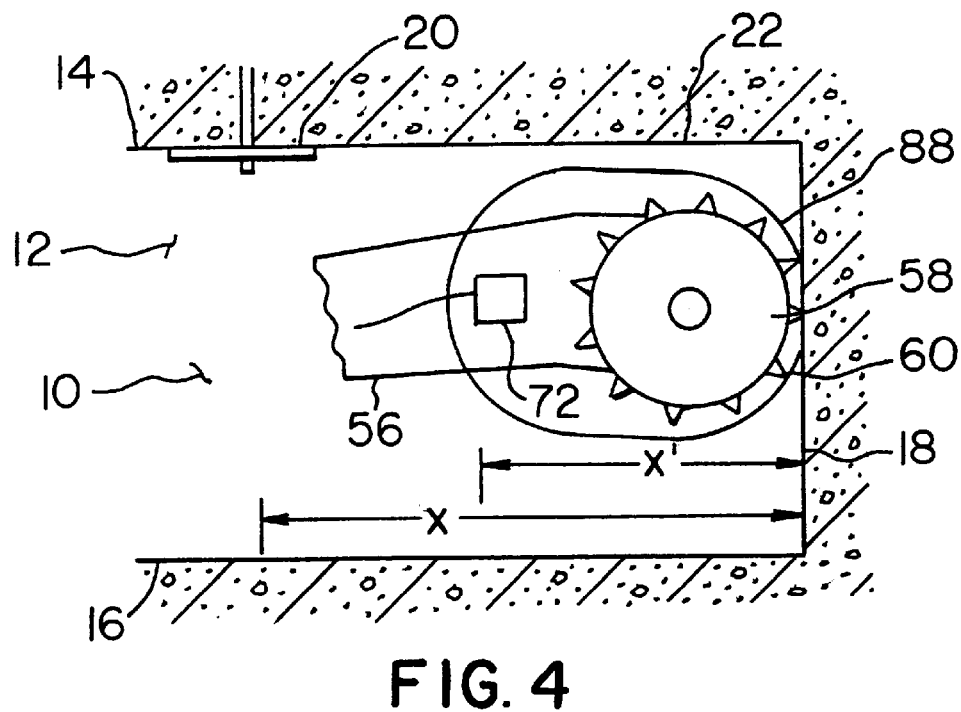
FIG. 4 is an elevation, partially in section, showing a portion of the continuous miner shown in FIG. 2 engaging with a mine face.

In operation, the continuous mining apparatus 42 is activated and guided through the mine shaft 10 of a mine by an operator located within the load-out vehicle 48. The continuous mining apparatus 42 forms a part of a continuous mining system for mining a material underground, such as coal. Hence, the continuous mining apparatus 42 is provided in the mine shaft 10, which includes a supported portion 20 and an unsupported portion 22. The rotary cutter head 58 is then placed against the mine face 18 as shown in FIG. 4. As is evident, the rotary cutter head 58 and the methane sensors 72 are positioned below an unsupported portion 22 of the mine roof 14. The methane sensors 72 are positioned a distance X' from the mine face 18 which is less than the distance X where the mine roof 14 is supported. The position of the methane sensors 72 should be within an envelope 88 having appropriate dimensions as determined in a case-by-case basis. The cutter bits 60 are then forced into the mine face 18 extracting coal therefrom, which then passes from the discharge conveyor 62 to the tramming conveyor 46, and then to the load-out vehicle 48.

As shown in FIG. 5, while operating the continuous miner 44 and mining coal, intermittent methane gas measurements, such as every minute or every twenty minutes, are taken from the methane sensors 72 which are positioned in an area near the mine face 18 in the unsupported portion 22 of the mine shaft 10. A signal passes along cables 82 to the microprocessor based controller 84 and the display 90 located in the load-out vehicle 48. The display 90 is electrically coupled to the sensors 72, 74, 76 and 78 through the controller 84. Preferably, the controller 53, the controller 84 and the display 90 are located in the load-out vehicle 48 which is at a remote location. Alternatively, methane gas measurements can be taken continuously. If the methane gas concentration level exceeds acceptable safe levels, say 2%, then power to the continuous miner 44 can be shut off either manually by the operator or automatically by computer controls. Since power to the continuous miner 44 is supplied from a different power line than the methane sensors 72, continual monitoring or detecting can take place adjacent the mine face 18. The methane sensors 72 also can monitor the mine face 18 if power to the continuous miner 44 is shut off for other reasons.

The air flow sensor 74, the oxygen sensor 76 and the carbon monoxide sensor 78 can likewise monitor intermittently or continuously. The sensors measure the atmospheric conditions near or adjacent to the mine face 18. This information measured from the sensors indicates whether it is safe for a miner 24 to go near the mine face 18 to inspect the area. After the continuous miner 44 is shut down due to high levels of methane gas, the ventilation tube 68 pumps or moves in fresh air and the scrubber 70 pumps out or moves out the methane gas laden air thereby reducing the methane gas levels in the mine shaft 10. Once the methane gas levels drop to or drop below an acceptable level, as detected by the methane sensors 72, the area can be inspected and/or electric power can be supplied to the continuous miner 44. Then, if the methane gas levels remain at or below acceptable levels, the rotary cutter head 58 can be engaged with the mine face 18 and mining resumed. If methane gas levels rise above the acceptable level prior to mining, then power to the continuous miner 44 is again shut off. The present invention eliminates the necessity of sending a miner 24 to the area near the continuous miner 44 to take methane gas measurements. This eliminates the possibility of exposing the miner 24 to a dangerous and explosive environment. Further, the present invention permits more accurate methane gas measurements to be taken for two reasons: (1) the methane gas sensor is positioned in close proximity to the mine face 18; and (2) the methane gas readings are taken on the fly, i.e., while the rotary cutter head 58 is engaged with the mine face 18. The prior art method of taking methane gas measurements requires the mining operation to cease during measurements, which is less accurate than taking the measurement on the fly, as well as dangerous to the miner 24. Further, the present invention permits continuous mining during a shift resulting in an increased yield per shift because the continuous miner 44 need not shut down every twenty minutes.

Also, the present invention is safer to operate than the prior art should methane gas levels reach unsafe levels. First, no human miner 24 needs to take measurements in close proximity to the mine face 18, whether it be in a supported portion 20 or an unsupported portion 22 of a mine roof 14. The present invention not only measures methane gas levels after power is shut off to the continuous miner 42, but also does not require a miner 24 to restart the continuous miner 44 in close proximity to the mine face 18.

The atmospheric detection system 40 of the present invention can be used in combination with a fire suppression system as disclosed in U.S. patent application Ser. No. 09/037,650, now U.S. Pat. No. 5,967,676, entitled "Fire Suppression System For An Automated Mining System" having inventors identified as Thomas W. McCormick, Danny L. Stickel, David A. Christopher, Patrick E. Retzer and Larry G. Offutt, filed concurrently herewith and incorporated by reference, as well as in combination with a continuous mining apparatus as disclosed in U.S. patent application Ser. No. 09/037,405, entitled "Electrical Control System For Apparatus And Method For Continuous Underground Mining" having inventors identified as Larry G. Offutt and David A. Christopher, filed concurrently herewith and incorporated by reference.

Having described the presently preferred embodiment of the invention, it is to be understood that it may otherwise be embodied within the scope of the appended claims.

We claim:

1. An atmospheric detection system for use in a mine, comprising:
   a continuous miner having a rotary cutter head attached to a frame and a motor for driving said rotary cutter head;
   a sensor adapted to sense an atmospheric condition mounted to said continuous miner and movable therewith;
   a first power line for supplying power to said motor;
   a controller coupled to said motor and said first power line for controlling rotation of said rotary cutter head at a remote location;
   a second power line for supplying power to said sensor;
   a display coupled to said sensor for displaying the sensed atmospheric condition at a location remote of said sensor;
   an exhaust fan provided on said continuous miner;
   an air flow sensor attached to said continuous miner for sensing an exhaust velocity of;
   an oxygen sensor attached to said miner; and
   a carbon monoxide sensor attached to said continuous miner, wherein said air flow sensor, said oxygen sensor and said carbon monoxide sensor are coupled to said display for displaying the atmospheric condition sensed at each of said sensor locations.

2. An atmospheric detection system for use in a mine as claimed in claim 1, wherein said sensor is positioned in close proximity to said rotary cutter head.

3. An atmospheric detection system for use in a mine as claimed in claim 1, wherein said rotary cutter head is rotatably coupled to a boom that is pivotally mounted to said frame.

4. An atmospheric detection system for use in a mine as claimed in claim 3, wherein said sensor is mounted to said boom.

5. An atmospheric detection system for use in a mine as claimed in claim 1, wherein said continuous miner includes means for moving said continuous miner along a mine floor.

6. An atmospheric detection system for use in a mine as claimed in claim 5, wherein said continuous miner further comprises a miner conveyor in flow communication with said rotary cutter head.

7. An atmospheric detection system as claimed in claim 6, further comprising a tramming conveyor coupled to said continuous miner, said tramming conveyor including a conveyor in flow communication with said miner conveyor, said tramming conveyor operatively coupled to said controller for controlling movement of said tramming conveyor along the mine floor and movement of said conveyor of said tramming conveyor.

8. An atmospheric detection system for use in a mine as claimed in claim 7, further comprising an operator station, said tramming conveyor comprising an inlet end positioned adjacent said miner conveyor and an outlet end positioned adjacent said operator station, said controller and said display positioned within said operator station.

9. An atmospheric detection system for use in a mine as claimed in claim 8, wherein said tramming conveyor is made up of a plurality of separately driven sections.

10. An atmospheric detection system for use in a mine as claimed in claim 1, wherein said sensor is adapted to sense methane.

11. An atmospheric detection system for use in a mine as claimed in claim 10, wherein said sensor intermittently senses for methane.

12. An atmospheric detection system for use in a mine as claimed in claim 10, wherein said sensor continuously senses for methane.

13. An atmospheric detection system for use in a mine as claimed in claim 10, wherein said continuous miner has a forward end and said sensor for sensing methane is positioned rearwardly of said forward end and said oxygen sensor, said carbon monoxide sensor and said air flow sensor are positioned rearwardly of said sensor for sensing methane.

* * * * *